United States Patent [19]

Mori et al.

[11] Patent Number: 4,578,112

[45] Date of Patent: Mar. 25, 1986

[54] CATALYTIC REACTION PROCESS

[75] Inventors: Toshikatsu Mori, Hitachi; Seizi Takeuchi, Hitachiota; Shimpei Matsuda, Tokai; Teruo Kumagi, Hitachi; Akira Kato, Hitachi; Hisao Yamashita, Hitachi; Masato Takeuchi, Katsuta, all of Japan

[73] Assignee: Hitachi, Ltd., Tokyo, Japan

[21] Appl. No.: 490,517

[22] Filed: May 2, 1983

Related U.S. Application Data

[63] Continuation-in-part of Ser. No. 347,721, Feb. 10, 1982, which is a continuation of Ser. No. 127,057, Mar. 4, 1980, abandoned.

[30] Foreign Application Priority Data

| Mar. 12, 1979 | [JP] | Japan | 54-29754 |
| Mar. 12, 1979 | [JP] | Japan | 54-29755 |
| Mar. 12, 1979 | [JP] | Japan | 54-29756 |
| Mar. 12, 1979 | [JP] | Japan | 54-29757 |
| Mar. 12, 1979 | [JP] | Japan | 54-29758 |
| Mar. 12, 1979 | [JP] | Japan | 54-29759 |

[51] Int. Cl.$^4$ .............................................. C22B 3/00
[52] U.S. Cl. ...................................... 75/108; 429/40; 429/42
[58] Field of Search ..................... 75/108; 429/40, 42

[56] References Cited

U.S. PATENT DOCUMENTS

| 3,553,022 | 1/1971 | Gregory | 429/42 |
| 3,799,811 | 3/1974 | Sampson | 429/42 |
| 3,956,014 | 5/1976 | Landsman | 429/42 |

Primary Examiner—Peter D. Rosenberg
Attorney, Agent, or Firm—Antonelli, Terry & Wands

[57] ABSTRACT

Disclosed is a catalytic reaction process in which a substance in a liquid reaction system is catalytically reacted with a gaseous substance which is hardly soluble in the liquid reaction system in the presence of a solid catalyst of a non-electroconductive, hydrophobic polymeric material, a part of the surface of which is non-compatible with the liquid reaction system or with the liquid reaction system and a product formed by the catalytic reaction.

According to this process, mild reaction conditions can be selected and adopted and separation or recovery of the catalyst can be remarkably facilitated. This catalytic reaction process can be applied to various liquid-gas reactions and can be applied especially advantageously to oxidation and reduction of organic substances and inorganic ions for disposal of waste waters and recovery of valuable substances.

10 Claims, No Drawings

CATALYTIC REACTION PROCESS

CROSS-REFERENCES TO RELATED APPLICATIONS

This is a continuation-in-part application of our prior U.S. Application, Ser. No. 347,721, filed Feb. 10, 1982 which, in turn, is a continuation application of prior application, Ser. No. 127,057, filed Mar. 4, 1980, abandoned.

BACKGROUND OF THE INVENTION (1) Field of the Invention

The present invention relates to a process in which a substance present in a liquid reaction system is reacted with a gaseous substance introduced from the outside in the presence of a catalyst. More particularly, the invention relates to a process in which catalytic reaction of a gaseous substance hardly soluble in a liquid is carried out in a liquid phase-solid phase-gas phase heterogeneous reaction system formed on the surface of a solid catalyst.

(2) Description of the Prior Art

The following techniques can be mentioned as the known technique using a water-repellent catalyst or adsorbent.

(1) Japanese Patent Application Laid-Open Specification No. 155492/75 entitled CATALYST FOR HEAVY WATER-HYDROGEN EXCHANGE discloses a hydrophobic catalyst comprising C-Pt-hydrophobic polymer.

(2) Japanese Patent Publication No. 32800/76 entitled PROCESS FOR EXCHANGE OF HYDROGEN ISOTOPES discloses a process for exchange of hydrogen isotopes in which a catalyst comprising at least one metal of the group VIII of the Periodic Table, which is sealed and coated with a gas-permeable or $H_2O$-impermeable material, is used.

(3) Japanese Patent Publication No. 41195/76 entitled PROCESS FOR EXCHANGE OF HYDROGEN ISOTOPES BETWEEN HYDROGEN GAS AND LIQUID WATER discloses a process in which hydrogen isotopes are concentrated by using a catalyst comprising an element of the group VIII of the Periodic Table supported on the surface of a polytetrafluoroethylene carrier.

(4) Japanese Patent Application Laid-Open Specification No. 156297/77 entitled PROCESS FOR EXCHANGE OF HYDROGEN ISOTOPES discloses a double-temperature exchange process in which hydrogen isotopes are exchanged between water and $H_2$ by contacting them in a counter-current manner with a catalyst having a film of a hydrophobic polymer.

(5) Japanese Patent Application Laid-Open Specification No. 4197/78 entield PROCESS FOR EXCHANGE OF HYDROGEN ISOTOPES discloses a process in which reaction is carried out in a mixed bed comprising a hydrophobic catalyst including a supported noble metal and a hydrophilic carrier, (6) U.S. Pat. No. 4,061,724 entitled CRYSTALLINE SILICA discloses a process in which organic materials are selectively adsorbed from water by using silica which has been rendered hydrophobic.

(7) Canadian Pat. No. 958,821 REDUCTION OXIDATION PROCESS AND APPARATUS.

(8) Canadian Pat. No. 959,628 REDUCTION OF POLYSULFIDE.

Both Canadian patents disclose oxidation and reduction process using a hydrophobic catalyst whose carrier or substrate is electronically conductive.

As the process for oxidizing ions or molecules in aqueous solutions, there are known: (a) a process in which a water-soluble strong oxidant, such as hydrogen peroxide or a permanganate, is used; (b) a process in which ozone gas is used; (c) a process in which an aqueous solution is contacted with an oxygen-containing gas in the presence of a catalyst (homogeneous metal ion catalyst); and (d) a process in which oxidation is biochemically performed by an aerobic microorganism, and various methods of these known techniques are practically carried out. However, these known techniques involve varous disadvantages. For example, oxidants used in the processes (a) and (b) are ordinarily expensive, and in the process (c), since a homogeneous system is employed, separation of the catalyst from the reaction product or starting reactant is very difficult.

When an oxidation reaction is carried out in an aqueous solution by using an oxygen-containing gas, since the amount of oxygen dissolved in water is very small, the oxidation speed is ordinarily very low. In a gas phase oxidation reaction using oxygen gas, for example, oxidation of hydrocarbons, it is known that the reaction is promoted and easily advanced by a solid catalyst, for example, platinum, manganese oxide or nickel oxide supported on alumina. Ordinary solid catalysts, however, can hardly be used in aqueous solutions or the solid catalysts lose the catalytic activity in aqueous solutions. It is apparent that the reason is that these ordinary solid catalysts are hydrophilic and their surfaces are wetted and covered with water in aqueous solutions. Therefore, oxygen gas acting as the oxidant is not allowed to reach the catalyst surface or the active points on the surface of the catalyst are covered with water molecules, with the result that the catalytic activity is not exerted.

As the process for reducing ions or molecules in an aqueous solution, there are known: (1) a process in which a water-soluble reducing agent, such as sodium sulfite, sodium sulfide or acidic stannous chloride, is used; (2) a process in which a powder of a metal producing hydrogen of the nascent state under acidic or alkaline conditions, such as zinc, aluminum or tin, is used; (3) a process in which a water-soluble reducing gas, such as hydrogen sulfide or sulfurous acid gas, is used; and (4) a process in which a reducing gas hardly soluble in water, such as hydrogen or carbon monoxide, is used. Methods of these techniques are practically carried out but these techniques involve defects. For example, in the processes (1), (2) and (3), undesirable by-products are formed in the reaction mixture liquids, reaction vessels are readily corroded, and the reducing agents used are expensive. Furthermore, in the process (4), since the reducing gas used is hardly soluble in water, high temperatures and high pressures are necessary for completion of the reaction. As means for eliminating this defect by increasing the reaction speed, there has been proposed a process in which a homogeneous catalyst system is used. According to this process, however, no substantial improvement is attained and separation of the catalyst from the reactants is very difficult. Furthermore, even if heterogeneous catalysts are used, since conventional solid catalysts are hydrophilic, the catalyst surface is covered with water and the reducing gas is hardly adsorbed on the catalyst surface, with the result that no substantial catalytic effect can be attained.

Various processes for promoting certain reactions by using water-repellent catalysts are known. A process for concentrating heavy water by the following isotope exchange reaction between water and hydrogen has recently been proposed:

$$H_2O(l) + HD(g) \rightleftharpoons HDO(l) + H_2(g)$$

It was reported that a platinum type catalyst which has been rendered water-repellent is effective for this reaction. As means for rendering such catalyst water-repellent, there have been proposed a process in which a hydrophilic $Pt-Al_2O_3$ or Pt-active carbon catalyst is coated with a silicone oil (see Japanese Patent Publication No. 32800/76) or with a polytetrafluoroethylene resin (see Japanese Patent Publication No. 41195/76 and Japanese Patent Application Laid-Open Specification No. 155492/75), and a process in which Pt is stuck to a water-repellent organic polymer (see Japanese Patent Publication No. 41195/76). As another process using a water-repellent catalyst, there are known a process in which oxygen and hydrogen formed while a secondary battery is used are reacted in the gas phase and converted to water (the catalyst is rendered water-repellent to prevent the catalyst from being wetted with splashes of an electrolyte) and a process in which hydrogen iodide (HI) is decomposed (it is reported that a water-repellent catalyst is used to reduce influences of steam present in the reaction system). Moreover, it has been reported that hydrophobic silica was developed as an adsorbent for adsorbing organic components in aqueous solutions (see U.S. Pat. No. 4,061,724). In a fuel cell, for example, a fuel cell of the oxygen-hydrogen system, an electrode acts also as a catalyst for promoting electron donating and accepting reactions of oxygen and hydrogen molecules, and such electrode plate is rendered water-repellent by coating with a polytetrafluoroethylene resin or the like to prevent an electrolyte from leaking into a gas chamber.

In Canadian Pat. No. 959,821 and No. 959,628, there are disclosed processes for oxidizing and reducing $N_2S$ or other substances by introducing an oxidizing gas or a reducing gas into a reaction system in the presence of a hydrophobic catalyst whose carrier or substrate is electrically conductive.

In the known processes, transportation or transfer of electrons which effect oxidizing and reducing reactions is carried out through the electronically conductive carrier or substrate.

The present inventors have found that reducing and oxidizing reactions surprisingly took place when a catalytically active, non-carbonaceous, porous ceramics or plastics is used; the catalyst being repellent or non-philic with respect to a liquid in a reaction system into which a reactive gas is introduced.

The carrier used in the cited Canadian patents are carbon, which are electro-conductive. On the other hand, in the present invention, the electroconductivity of the carrier is an undesirable characteristic because the reaction is limited to the area where three phases (gas-liquid-solid) are formed on the surface of the catalysts. If the carrier is conductive, electrons generated as a result of chemical reaction are absorbed in the carrier whereby the activity of the catalyst is lowered. Accordingly, the present invention employs the catalysts having a non-electroconductive carrier.

SUMMARY OF THE INVENTION

It is a primary object of the present invention to provide a process in which a substance in a liquid containing reaction system is easily catalytically reacted with a gaseous substance which is hardly soluble in said liquid.

Another object of the present invention is to provide a catalytic reaction process in which structures of molecules and/or ions in an aqueous solution are changed in the presence of a hardly soluble gas by oxidation on reduction reaction.

The present invention is characterized in that a substance present in a liquid containing reaction system and a gaseous substance hardly soluble in said liquid are contacted with a catalyst of which the carrier is non-electroconductive, hydrophobic polymeric porous solid material in said liquid containing reaction system, a part of the surface of said catalyst being non-compatible with said liquid so that the substance in said liquid and said gaseous substance are allowed to fall in contact with a catalytic component of said catalyst, whereby at least one of said substances is chemically converted.

We conceived an idea of a novel reaction process for reacting a substance in a liquid reaction system with a gas which is hardly soluble in the liquid by forming a heterogeneous system capable of advancing this reaction very easily, and found that this heterogeneous system can be formed in a catalyst of a non-electroconductive, hydrophobic, porous material having a solid surface which is non-compatible with the liquid. Based on this finding, we have now completed the present invention.

In the instant specification, by the term "non-compatible with the liquid," it is meant that the surface of the solid has such a property that the surface of the solid is not completely wetted with the iquid and only a discontinuous film of the liquid is formed on the surface of the solid.

According to the present invention, by virtue of this specific property of the solid catalyst, three phases; that is, a liquid phase, a gas phase and a solid phase, are simultaneously formed on the surface of the catalyst, and it is considered that the reaction gas is allowed to readily arrive at active points of the catalyst and advance of the reaction is promoted.

DETAILED EXPLANATION OF THE INVENTION

The present invention will now be described in detail mainly with reference to embodiments where the present invention is applied to an oxidation reaction, for facilitating the understanding of the present invention.

Water soluble organic and inorganic ions and molecules are mentioned as substances that are oxidized according to the oxidation process of the present invention. As the organic substance, there can be mentioned, for example, organic acids; e.g., acetic acid, formic acid, sulfur-containing compounds such as mercaptans, sulfides and polysulfides; e.g., disulfides and organic compounds containing halogens, metals or phosphorus. These organic compounds are present in aqueous solutions in the form of ions formed by dissociation. As the inorganic substance, there can be mentioned, for example, ions of metals capable of having at least two different valencies, such as transition metal ions; e.g., $Fe^{II}$, $Cu^{I}$ and $Cr^{II}$, ions of metal oxyacid salts such as $VO^{++}$, ions of oxyacids of Mo, Cr, W and Mn, nitrogen-containing ions such as $NH_4^+$ and $NO_2^-$, sulfur-containing ions such as $S^{--}$, $SH^{--}$, $S_2O_3^{--}$, $S_2O_6^{--}$ and $SO_3^{--}$, and complex compounds and halides of various metals.

As typical instances of the oxidative gas that is used in the oxidation process of the present invention, there can be mentioned oxygen, air, nitrogen monoxide, nitrogen dioxide, nitrogen suboxide and sulfur dioxide gas. Of these gases, use of oxygen, oxygen-containing gas and air are preferred from the economical viewpoint.

The reason for the use of a solid catalyst in the present invention is not only that the heterogeneous reaction is established by the use of a solid catalyst, but also that the use of a solid catalyst is advantageous over the use of a catalyst which is dissolved in a solution with respect to regeneration of the catalyst, handling of the catalyst and disposal of the waste water or reaction liquid. Ordinarily, heavy metals are mainly used as cataytic components, and if these heavy metal ions are dissolved in treating liquids, the post treatment and regeneration become difficult.

The water-repellent solid catalyst that is used in the oxidation process of the present invention is characterized in that at least a part of the surface of the catalyst has such a water-repellent property that all the surface thereof is not completely wetted or covered with a liquid in an aqueous solution but a gas phase can be formed on the surface thereof. Such water-repellent catalyst can be formed by subjecting a hydrophilic catalyst to a water-repellent carrier or preparing a shaped article from a mixture of a hydrophilic substance and a water-repellent substance.

As a carrier for the catalyst, there can be used non-electroconductive, hydrophobic porous particles and shaped articles of various polymers, such as polytetrafluoroethylene, polyethylene, polypropylene, polystyrene, cross-linked polystyrene and polymethyl methacrylate.

Catalytic components customarily used for gas phase oxidation reaction can be used for the catalytic active component of the water-repellent catalyst of the present invention. As typical instances of the catalytic component, there can be mentioned elements of the group VIII of the Periodic Table (Fe, Co, Ni and metals of the platinum group such as Pt, Pd, Ru, Rh, Ir and Os), elements of the group V of the Periodic Table (such as V, Nb, As and Bi), elements of the group VIA (such as Cr, Mo, W and U), elements of the group IV (such as Ti, Sn and Pb), elements of the group IB (such as Cu, Ag and Au) and elements of the group IIB (such as Zn, Cd and Hg). These elements are used for the reaction in the form of metals, oxides, sulfates or halides. Furthermore, active alumina, silica alumina and zeolite may be used as the catalytic active component. The prepared water-repellent catalyst may be used after it has been activated by a reducing treatment.

The present invention can also be applied to an aqueous solution containing a small amount of an organic substance which is homogeneously incorporated (dissolved) in water. For example, according to the present invention, a substance contained in an aqueous solution containing about 20% of acetic acid, formic acid, or the like, can be oxidized in the presence of a water-repellent catalyst mentioned above. The abovementioned organic substance, such as methanol, increases the oleophilic property of the aqueous solution but, since inherent properties of water are strongly manifested in the aqueous solution, such aqueous solution is repelled by a water-repellent catalyst, for example, a catalyst treated with polytetrafluoroethylene.

Ordinary reaction vessels of the fixed bed type, fluidized bed type and suspended bed type can be used for oxidizing substances in aqueous solutions according to the oxidation process of the present invention. Furthermore, contact of an aqueous solution with an oxidative gas may be performed in a countercurrent manner or a concurrent manner or may be performed batchwise. The shape of the water-repellent catalyst is not particularly critical in the present invention. For example, there can be used fine particles having a size of 0.01 to 1 mm, spherical, columnar and cylindrical pellets having a size of 1 to 10 mm and honeycomb and plate-like shaped articles having a larger size.

When the oxidation process of the present invention is actually carried out, the dispersion state of the aqueous solution often becomes bad, and a particular contrivance is required in such case, especially when a fixed bed is used. In such case, good results are obtained when a catalyst bed is formed by mixing a water-repellent catalyst with a hydrophobic carrier.

In practicing the oxidation process of the present invention, the lower limit of the reaction temperature is the temperature of solidification of water, and the upper limit of the reaction temperature is determined depending on the heat resistance of the water-repellent substance. The reaction pressure is not particularly critical, but the reaction can be carried out under a pressure of 0.1 to 1,000 atmospheres, preferably 0.5 to 100 atmospheres.

The present invention can also be applied to the reducing process. In this embodiment, organic and inorganic ions present in water can be reduced. As examples of the organic substance, there can be mentioned organic acids; e.g., acetic acid, formic acid nitrogen-containing compounds, such as nitro compounds, sulfur-containing compounds, such as mercaptans and sulfides; e.g., thiophene, and organic compounds containing halogens, metals, phosphorus or the like. As the inorganic substance, there can be mentioned, for example, ions of metals having two or more different valencies, such as $Fe^{3+}$, $Cu^{2+}$, $Cr^{5+}$ and other transition metal ions, ions of metal oxyacids such as $VO^{2+}$, $CrO_4^{2-}$ and $WO_4^{2-}$, nitrogen-containing ions such as $NO_3^-$ and $NO_2^-$, sulfur-containing ions such as $SO_4^{2-}$ and $S_2O_6^{2-}$, and complex compounds of metals.

As typical instances of the reducing gas that is used in the present invention, there can be mentioned hydrogen, carbon monoxide, nitrogen monoxide, methane and nitrogen suboxide. These gases may be used singly or in combination with diluent gases. A mixture containing a plurality of reducing gases, such as synthesis gas, can be used in the present invention without any trouble.

At least a part of the surface of the water-repellent catalyst that is used in the present invention has such a water-repellent property that in an aqueous solution, all the surface of the catalyst is not completely wetted or covered with the aqueous solution and the reducing gas can be contacted with or adsorbed on the surface of the catalyst. Such water-repellent catalyst may be prepared according to the above-mentioned methods. Furthermore, the carrier, water-repelling agent and catalytic component for such water-repellent catalyst and reaction conditions are as described hereinabove.

Another application of the present invention resides in modification and addition reactions of organic compounds by utilizing a water-repellent and oil-repellent catalyst. By the term "water-repellent and oil-repellent catalyst" is meant a catalyst characterized in that at least a part of the surface of the catalyst has such water-repellent and oil-repellent properties that all the surface of the catalyst is not completely covered with water, solvent or reaction product but a gas phase can be formed on the surface of the catalyst. As the carrier of the water-repellent and oil-repellent catalyst, there can be used, for example, particles and shaped articles of organic polymers, such as polytetrafluoroethylene, polyethylene, cross-linked polystyrene and polymethacrylate, and particles and shaped articles coated with these materials.

Any water repellent agents having a critical surface tension which is larger than that of water (73 dynes/cm) can be used in the present invention.

As will be apparent from its name, the water-repellent and oil-repellent catalyst has no affinity with either water or an oil. Characteristics of this catalyst will now be described with reference to two embodiments.

In a first embodiment, the solution is water-methanol and the reacting gas is carbon monoxide. In this reaction, the product is acetic acid. When a conventional hydrophilic or water-repellent catalyst is used for this reaction, of which surface is wetted with water or methanol, carbon monoxide is not allowed to arrive at the surface of the catalyst and the speed of advance of the reaction is very low. In a second embodiment, the solution is water and the reacting gas is ethylene, In this reaction, the product is ethanol. Also in this embodiment, the surface of a hydrophilic or water-repellent catalyst is wetted with water or formed methanol and, therefore, the speed of advance of the reaction is very low. On the other hand, when the water-repellent and oil-repellent catalyst of the present invention is applied to these two reactions, since the catalyst has a property of strongly repelling water, acetic acid, methanol and ethanol, carbon monoxide and ethylene gas which are hardly soluble in water are allowed to easily arrive at the surface of the catalyst and the reactions are remarkably promoted. Accordingly, the water-repellent and oil-repellent catalyst of the present invention is very effective for reactions of organic substances having a relatively large surface tension. Therefore, in order to utilize the activity of the water-repellent and oil-repellent catalyst most efficiently, it is necessary to select a catalyst having a critical surface tension lower than the surface tension of the starting reaction liquid and the surface tension of the reaction product liquid. It is preferred that the critical surface tension of the catalyst be lower than 20 dyn/cm as measured at 20° C. Furthermore, it is preferred that the contact angle of the catalyst to water be larger than 90° and that the catalyst carrier should have fine pores and a large specific surface area. The oil-repellency of the catalyst can be provided by more strongly treating the catalyst with a water-repellent agent than the case of providing water-repellency. This is performed by treating the water-repellent catalyst which supports catalytic components thereon with the same water-repellent agent. The oil-repellency can be regarded as water-repellency, these terms being the matter of strength of water repellency. The oil-repellency is provided for lowering the sticking of oily products to the catalyst.

Catalytic components customarily used for gas phase reaction can be used for the catalytic active component of the water-repellent and oil-repellent catalyst of the present invention. As typical instance of the catalytic component, there can be mentioned elements of the group VIII of the Periodic Table (Fe, Co, Ni and metals of the platinum group such as Pt, Pd, Ru, Rh, Ir and Os), elements of the group V of the Periodic Table (such as V, Nb, As and Bi), elements of the group VIA (such as Cr, Mo and W), elements of the group IV (such as Ti, Sn and Pb), elements of the group IB (such as Cu, Ag and Au) and elements of the group IIB (such as Zn, Cd and Hg). These elements are used for the reaction in the form of metals, oxides, sulfates and chlorides. These active components are supported singly or in combination by mixing, lamination or impregnation. The active metal is supported in an amount of 0.01 to 10% by weight, based on the weight of the carrier, as the metal atom. The shape of the water-repellent and oil-repellent catalyst is not particularly critical in the present invention. For example, fine particles having a size of 0.01 to 0.1 mm, spherical, columnar and cylindrical pellets having a size of 1 to 10 mm and honeycomb and plate-like shaped articles having a larger size can be used.

Whether the water-repellent coating layer can come into the interior of the carrier depends on the size of micropores of the carrier used and a particle size of a water-repellent agent. The micropore size of the teflon used in the present invention is 1 to 10 micron meters, fine particles of teflon in the dispersion (particle size: 0.4 micron on average) can come into the inner portion of the carrier.

In the present invention, a solution or liquid is involved in the reaction. Accordingly, the micropore size of the carrier should preferably be not smaller than 0.1 micrometer. A more preferable range of the pore size is 1 to 10 micrometers (microns).

Examples of the preparation of the water-repellent and oil-repellent catalyst of the present invention will now be described.

Catalyst Preparation Process (I)

Porous polytetrafluoroethylene having a square shape having a side of 5 mm and a thickness of 1 mm was dried at 120° C. for 2 hours and then deaerated. Then, the polytetrafluoroethylene was impregnated with a liquid mixture of chloroplatinic acid and acetone, dried and reduced for 3 hours in a hydrogen current at 200° to 240° C. to form a catalyst having Pt supported in an amount of 0.5% by weight based on the carrier.

Catalyst Preparation Process (II)

The catalyst prepared in the process (I) was dipped in a polytetrafluoroethylene suspension (marketed under tradename "Polyflon Liquid") to render the catalyst water-repellent and oil-repellent.

Catalyst Preparation Process (III)

The catalyst prepared in the process (I) was thrown into a solution of copper sulfate having a concentration of 0.1 mole/l and wet-reduced for one hour while introducing hydrogen gas into the solution. The reduced catalyst was dried and then similarly reduced in a solution of chloroplatinic acid. In the resulting catalyst, Pt and Cu were supported in amounts of 0.6% by weight and 0.05% by weight, respectively, based on the carrier.

Catalyst Preparation Process (IV)

The catalyst prepared in process (I) was rendered water-repellent by dipping it in Polyflon Liquid.

The above-mentioned processes (I) to (IV) are ordinary processes for preparing water-repellent and oil-repellent catalysts. A carrier is selected from organic polymeric materials, such as mentioned above. An active component is selected from the above-mentioned active metals. As described above, with respect to the preparation process (III), different metals may be supported by lamination or mixing. Furthermore, the hydrophilic property imparted by deposition of an active metal may be reduced by using, not only the water-repelling agent described above with reference to the preparation processes (II) and (IV), but also silicone compounds.

Most Preferred Modes for Practice of the Invention

The presnt invention will now be described in detail with reference to the following Examples and Comparative Examples.

EXAMPLE 1

This example illustrates oxidation of $Na_2V_2O_5$ formed by liquid phase reduction of ammonium metavanadate ($NH_4VO_3$).

A porous divinylbenzene-styrene copolymer was used as a water-repellent carrier and was impregnated with an acetone solution of nickel nitrate to form a catalyst containing 3% by weight of nickel.

In a beaker was charged 200 ml of a solution containing 0.5 mole/l of $Na_2V_2O_5$, and 10 ml of the above catalyst was added to the solution. Air was introduced into the solution at a flow rate of 1 l/min at 55° C. in the form of fine bubbles. After passage of one hour, $NaVO_3$ was analyzed and it was found that the yield of $NaVO_3$ was higher than 90%.

EXAMPLE 2

This example illustrates oxidation of sulfurous ions ($SO_3^{--}$) to sulfuric ions.

Porous polytetrafluoroethylene having a porosity of 80% was impregnated with an acetone solution of palladium acetate, dried and reduced with hydrogen to form a catalyst containing 0.2% by weight of Pd.

To 200 ml of a solution containing 1 mole/l of sodium sulfite was added 10 g of the above catalyst, and oxygen was supplied into the solution at a feed rate of 1 l/min for two hours through a ball filter.

The yield of sulfuric ions was 63% at 50° C. or 94% at 80° C.

EXAMPLE 3

A porous polytetrafluoroethylene square plate having a side of about 5 mm and a thickness of about 1 mm was impregnated with an ethanol solution of chloropatinic acid, dried at 100° C. for two hours and reduced with hydrogen at 200° C. for two hours to obtain a polytetrafluoroethylene catalyst supporting 0.5% by weight of platinum.

An absorbing bottle was charged with 100 ml of an aqueous solution of ammonium hydrosulfide having a concentration of 0.1 mole/l and 20 ml of the above catalyst, and oxygen gas was fed into the solution at a flow rate of 200 ml/min at 80° C. to effect oxidation. The ratio of reduction of the amount of ammonium hydrosulfide was 87% when the reaction was conducted for one hour.

COMPARATIVE EXAMPLE 1

Ammonium hydrosulfide was oxidized under the same conditions as described in Example 3 except that alumina particles having a diameter of 33 mm were used instead of the polytetrafluoroethylene plate. The ratio of reduction of the amount of ammonium hydrosulfide was 7%.

EXAMPLE 4

This example illustrates reduction of sodium sulfate ($Na_2SO_4$) with hydrogen.

A glass reaction vessel having an inner capacity of 1 liter was charged with 100 ml of an aqueous solution of sodium sulfate having a concentration of 0.1% mole/l, and 20 ml of a catalyst formed by supporting 1% by weight of platinum on a carrier obtained by slicing a polytetrafluoroethylene tube having an outer diameter of 5 mm and an inner diameter of 3 mm was added to the aqueous solution. Hydrogen was fed into the solution at a feed rate of 200 ml/min and reaction was carried out at a temperature of 150° C. under a pressure of 5 kg/cm$^2$G for two hours. The ratio of reduction of sodium sulfate to sodium sulfite was 6.1%. Incidentally, the theoretical value of the reduction ratio, calculated from the free energy change of the reaction, was 6.7%.

COMPARATIVE EXAMPLE 2

Reduction of sodium sulfate was carried out in the same manner as described in Example 4 except that a catalyst formed by supporting 1% by weight of Pt on an alumina Rashig ring (cylinder), which had the same size as that of the polytetrafluoroethylene tube used in Example 10, was used. The reduction ratio was lower than 0.01%.

EXAMPLE 5

An experiment of reduction of acetone ($CH_3COCH_3$) in an aqueous solution was carried out.

A porous divinylbenzene-styrene copolymer was impregnated with an acetone solution of chloroplatinic acid, dried and reduced with hydrogen at 200° C. to form a water-repellent catalyst containing about 0.3% by weight of platinum.

A beaker was charged with 200 ml of an aqueous solution containing 1% by weight of acetone, and 10 ml of the above catalyst was added to the solution. Hydrogen gas was circulated into the solution at a rate of 500 ml/l in the form of fine bubbles through a ball filter. Reaction was carried out at 70° C. for two hours. The yield of isopropyl alcohol was 68%.

EXAMPLE 6

Porous polytetrafluoroethylene having a cylindrical shape having an outer diameter of 8 mm, an inner diameter of 5 mm and a length of 8 mm was used as a catalyst carrier. An aqueous solution of chloroplatinic acid was diluted with isopropyl alcohol and the porous polytetrafluoroethylene carrier was impregnated with the dilution. The impregnated carrier was dried and reduced in a nitrogen current at 200° C. for five hours to obtain a water-repellent catalyst containing 0.5% by weight of platinum.

An experiment of precipitation of copper from a solution of copper nitrate was carried out in the following manner.

A vessel was charged with about 300 ml of a solution containing 1 mole/l of copper nitrate, and about 30 g of the above catalyst was thrown into the solution. Hydrogen gas was circulated in the solution at a flow rate of 500 ml/min through a ball filter, and reaction was carried out at 50° C. for three hours. By analysis of the residual copper concentration in the solution, it was found that more than 90% of copper contained in the solution was deposited on the water-repellent catalyst.

COMPARATIVE EXAMPLE 3

An experiment was carried out in the same manner as described in Example 6 except that porous polytetraluoroethylene alone was used. By the naked eye observation, it was found that copper was not deposited on the polytetrafluoroethylene. Also by analysis of the copper concentration in the solution, it was confirmed that copper ions had not been reduced.

COMPARATIVE EXAMPLE 4

An experiment was carried out in the same manner as described in Example 6 except that a commercially available alumina catalyst containing 0.5% by weight of platinum (hydrophilic catalyst) was used. By analysis of the copper concentration after the reaction, it was found that the ratio of reduction of the amount of copper ions was lower than 5%.

EXAMPLE 7

A porous polytetrafluoroethylene plate (2 cm × 2 cm; 1.5 mm in thickness) was impregnated with nickel by using a solution of nickel nitrate in water-propanol, and the plate was then dried and reduced at 200° C. for 10 hours with hydrogen to obtain a water-repellent catalyst containing about 5% by weight of nickel.

The above catalyst was added to a solution containing 0.1 mole/l of chloroplatinic acid, and hydrogen gas was dispersed and circulated in the solution at 50° C. for two hours. Platinum was deposited on the catalyst in an amount of 0.05 g per gram of the water-repellent catalyst. The catalyst obtained in this example could be effectively used as an electrode of a fuel cell.

EXAMPLE 8

To a liquid mixture of 200 ml of water and 20 ml of methanol was added 30 g of a catalyst prepared according to the catalyst preparation process (II) described hereinabove. The resulting solution was charged in a high pressure reaction vessel equipped with a reflux cooler and oxygen was fed at a rate of 1 l/min. The reaction temperature and pressure were controlled to 120° C. and 15 kg/cm$^2$, respectively. After the reaction had been conducted for two hours, formaldehyde and formic acid were analyzed. It was found that the yields of formalin and formic acid were 60% and 12%, respectively, based on the initial amount of methanol.

COMPARATIVE EXAMPLE 5

Oxidation of methanol was carried out in the same manner as described in Example 8 except that the catalyst was not added while oxygen alone was introduced. Each of the yields of formalin and formic acid was lower than 1%.

EXAMPLE 9

This example illustrates oxidation of ethanol in an aqueous solution.

The same catalyst as used in Example 8 was used in this example with the exception that the teflon carrier supporting platinum is further treated with a teflon dispersion liquid to provide oil-repellency. This process is in accordance with Catalyst Preparation Process (I).

To 200 ml of water was added 20 ml of ethanol, and 30 g of the catalyst was added to the solution. The reaction was carried out for two hours under the same conditions as described in Example 26. When acetaldehyde and acetic acid were analyzed, it was found that each of the yields of acetaldehyde and acetic acid was about 20%.

COMPARATIVE EXAMPLE 6

Oxidation of ethanol was carried out under the same conditions as described in Example 9 except that the catalyst was not added while oxygen alone was introduced. Each of the yields of acetaldehyde and acetic acid was lower than 1%.

EXAMPLE 10

Polytetrafluoroethylene tubes each having an outer diameter of 3 mm, an inner diameter of 2 mm, a length of 100 mm, and a porosity of 50% were impregnated with an acetone solution of chloroplatinic acid.

The tubes were then dried at 100° C. and subjected to a reducing treatment in a hydrogen gas stream at 200° C. to produce tabular catalysts containing 1% by weight.

Twenty of the catalysts were packed in a glass tube having an inner diameter of 30 mm. An aqueous solution of formic acid whose concentration is 0.1% mol/l was poured into the glass tube packed with the catalysts at a rate of 10 cc/minute. Further, air was supplied into the glass tube from the bottom thereof at a rate of 0.5 Nl/minute, while keeping the glass tube at 80° C. to carry out an oxidation reaction. 21% of formic acid was converted to carbon dioxide.

COMPARATIVE EXAMPLE 7

A cylindrical tube of cordilite having an outer diameter of 3 mm, an inner diameter of 2 mm and a length of 100 mm was impregnated with an aqueous solution of chloroplatinic acid to produce a catalyst whose platinum content was 1% by weight in the manner described in Example 10.

The oxidation reaction of formic acid was carried out using the catalyst in the same manner as described in Example 10. 5.1% of formic acid was converted into carbon dioxide.

What we claim is:

1. A catalytic reaction process for oxidizing S$^{--}$ or HS$^-$ in an aqueous solution, which comprises contacting an aqueous solution containing S$^{--}$ or HSA$^-$ ions with an oxidative gas in the presence of a catalyst which is solid in the aqueous solution, said solid catalyst consisting essentially of a non-electroconductive, porous carrier of a hydrophobic polymeric material and a catalytic component containing a metal element having a catalytic activity to S$^{--}$ or HS$^-$ in the aqueous solution in the presence of the oxidative gas, wherein a water-repellant agent capable of forming a discontinuous film of the aqueous solution on the surface of the solid catalyst is made co-present with the catalytic component so that said oxidative gas is allowed to arrive at active sites of the catalytic component together with the ions to oxidize the ions.

2. A catalytic reaction process for precipitating metal ions in an aqueous solution to form a metal from said ions, which comprises contacting a metal ion-containing aqueous solution with a reducing gas in the presence of a solid catalyst that consists essentially of a non-electroconductive, porous carrier of a hydrophobic polymeric material and a catalytic component containing a metal element having a reducing activity for said metal ions, wherein the solid catalyst has water-repellant properties, thereby to reduce the metal ions and to deposit the metal on the surface of said catalyst.

3. A catalytic reaction process according to claim 1, characterized in that the oxidative gas is oxygen or an oxygen-containing gas.

4. A catalytic reaction process according to claim 2, characterized in that the reducing gas is hydrogen or a hydrogen-containing gas.

5. A catalytic reaction process according to claim 2, wherein the catalytic component of the solid catalyst is impregnated within the water-repellent and oil-repellent carrier.

6. A catalytic reaction process according to claim 1, wherein said solid catalyst consists essentially of the catalytic component impregnated within the porous carrier of a water-repellant organic polymeric material and a water-repellant agent coated on the solid catalyst.

7. A catalytic reaction process according to claim 1, wherein said porous carrier is selected from the group consisting of polytetrafluoroethylene, polyethylene, polypropylene, polystyrene, cross-linked polystyrene and polymethyl methacrylate.

8. A catalytic reaction process according to claim 7, wherein said catalytic component is selected from the group consisting of a metal element of groups VIII, V, VIA, IV, IB and IIB.

9. A catalytic reaction process according to claim 2, wherein said reducing gas is selected from the group consisting of hydrogen, carbon monoxide, nitrogen monoxide, methane, nitrogen suboxide and a mixture thereof.

10. A catalytic reaction process according to claim 2, wherein said porous carrier is selected from the group consisting of polytetrafluoroethylene, polyethylene, polypropylene, polystyrene, cross-linked polystyrene and polymethyl methacrylate.

* * * * *